(12) United States Patent
Djian et al.

(10) Patent No.: US 7,521,218 B2
(45) Date of Patent: Apr. 21, 2009

(54) KERATINOCYTE CULTURING METHOD AND THE USE THEREOF

(75) Inventors: Philippe Djian, Paris (FR); Amandine Laetitia Vanessa Vanhoutteghem, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 111 days.

(21) Appl. No.: 10/564,964

(22) PCT Filed: Jul. 15, 2004

(86) PCT No.: PCT/FR2004/001864
§ 371 (c)(1), (2), (4) Date: Oct. 26, 2006

(87) PCT Pub. No.: WO2005/010173
PCT Pub. Date: Feb. 3, 2005

(65) Prior Publication Data
US 2008/0124356 A1  May 29, 2008

(30) Foreign Application Priority Data
Jul. 18, 2003 (FR) .................................. 03 08781

(51) Int. Cl.
*C12N 7/00* (2006.01)
*C12N 5/00* (2006.01)
*C12N 5/06* (2006.01)

(52) U.S. Cl. ..................... 435/235.1; 435/408; 435/349

(58) Field of Classification Search .................... None
See application file for complete search history.

(56) References Cited

U.S. PATENT DOCUMENTS 5,759,552 A * 6/1998 Paoletti et al. ........... 424/199.1
6,001,369 A   12/1999 Cochran et al.
6,114,168 A * 9/2000 Samarut et al. ............. 435/405

FOREIGN PATENT DOCUMENTS

| EP | 0 496 135 | 7/1992 |
| EP | 0 703 294 | 3/1996 |
| EP | 0 748 867 | 12/1996 |
| EP | 0 770 677 | 5/1997 |
| EP | 0 779 359 | 6/1997 |
| EP | 1 064 947 | 1/2001 |
| EP | 1 149 899 | 10/2001 |

OTHER PUBLICATIONS

Vanhoutteghem et al (Differentiation 72: 123-137, Apr. 2004; cited in IDS).*
ATCC Cell Lines and Hybridomas, 8th edition, 1994, p. 534.*
Xi et al (Journal of Reproduction and Development 49: 213-219, 2003).*
Beele, H. et al., "In vitro culture of chick down feather bulbi: A tool to obtain proliferating and differentiating keratinocytes in an organotypic structure", Experientia, vol. 46, No. 10, pp. 1053-1057, 1990.
Meyers, Craig et al., "Synthesis of Infectious Human Papillomavirus Type 18 in Differentiating Epithelium Transfected with Viral DNA", Journal of Virology, vol. 71, No. 10, pp. 7381-7386, Oct. 1997.
Abujoub, Amin et al., "Development of a Sustainable Chick Cell Line Infected with Marek's Disease Virus", Virology, vol. 214, No. 2, pp. 541-549, 1995.
Vanhoutteghem, Amandine et al., "Serial cultivation of chicken keratinocytes, a composite cell type that accumulates lipids and synthesizes a novel beta-keratin", Differentiation, vol. 72, No. 4, pp. 123-137, 2004.

* cited by examiner

*Primary Examiner*—Mary E Mosher
(74) *Attorney, Agent, or Firm*—Oblon, Spivak, McClelland, Maier & Neustadt, P.C.

(57) ABSTRACT

The invention relates to keratinocyte culture, a keratinocyte culturing method and the use thereof for spreading living attenuated viruses. The inventive method makes it possible to obtain living attenuated viruses and vaccines containing said viruses.

17 Claims, 9 Drawing Sheets

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
agtggattct atggacctgc                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic DNA

<400> SEQUENCE: 2
aactgagcag cttgctggc                                               19

<210> SEQ ID NO 3
<211> LENGTH: 19
<212> TYPE: DNA
<213> ORGANISM: Artificial Sequence
<220> FEATURE:
<223> OTHER INFORMATION: Synthetic DNA

<400> SEQUENCE: 3
cagtccaggt acgaagagc                                               19

<210> SEQ ID NO 4
<211> LENGTH: 20
<212> TYPE: DNA
<213> ORGANISM: Artificial Sequence
<220> FEATURE:
```

```
<223> OTHER INFORMATION: Synthetic DNA

<400> SEQUENCE: 4
taggatcggg atatggaagc                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
ggctttgatg ctatctgtgc                                              20

<210> SEQ ID NO 6
<211> LENGTH: 19
<212> TYPE: DNA
<213> ORGANISM: Artificial Sequence
<220> FEATURE:
<223> OTHER INFORMATION: Synthetic DNA

<400> SEQUENCE: 6
gtggagtctg acatcaacg                                               19

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
agaactgaga cgcacgatgc                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
actaggatgt tactgcgtgg                                              20
```

KERATINOCYTE CULTURING METHOD AND THE USE THEREOF

The present invention relates to a novel keratinocyte culture medium, to a method of culturing keratinocytes and to the use of this method for propagating live attenuated viruses. The live attenuated viruses obtained by this method and the vaccines comprising them constitute another subject of the invention.

A certain number of pathogenic viruses can completely replicate only in keratinocytes, because specific keratinocyte proteins are essential to their replication.

This is the case, for example, for MDV (Marek's disease virus) and for FPV (fowl pox virus).

The cells currently used for propagating the MBV virus are generally fibroblasts. The chicken fibroblasting culture used for the production of vaccines against MDV do not provide the production of free viral particles: the infection is semi-productive. Attempts have been made to try to establish continuous lines capable of productive infection, but without success (Abujoub et al., Virology, 214, 541-549, 1995). Because of the incomplete nature of the viral replication in fibroblasts, the cellular vaccines must necessarily be used in a form frozen in liquid nitrogen. As the virus produced by the fibroblasts lacks a complete envelope, it is neither cytolytic nor infectious.

In the case of Marek's disease, the animal is infected via the respiratory pathway. A short time after contamination, a cytolytic infection of B lymphocytes develops, the consequence of which is a cellular viremia which results in the latent infection of many tissues. Among the cell types infected are T lymphocytes, which will subsequently become transformed and produce lethal lymphomas. The virus is also transported to the epidermis, into the feather follicles which represent the only site of production of viruses having a complete envelope. The virus is present at very high titers in the cornified cells (squamae) of the superficial part of the epidermis, in particular in the feather follicles. The cells desquamate and infect other animals by inhalation of the squamae (Calnek et al., J. Natl. Cancer Inst., 45, 341-351, 1970; Calnek et al., Avian Dis., 14, 219-233, 1970; Carrozza et al., Avian Dis. 17, 767-781, 1973). Many vaccines have been developed since Marek's disease is a disease that is present throughout the world and responsible for heavy losses in the poultry farms affected. These vaccines consist of a suspension of chicken fibroblasts infected in culture with attenuated strains of the Marek's disease virus. The vaccines are prepared by freezing, in liquid nitrogen, of the live cells in culture medium containing cryoprotective agents. Immunization is carried out either by injection in ovo, or by subcutaneous injection one day after birth. The immunization protects against lymphoproliferative syndrome, but not against the keratinocyte infection. This explains the continuous persistence and transmission of the virus. Rapid mutations of the virus due to its persistence result in the appearance of increasingly virulent forms resistant to the existing vaccines.

Human papilloma viruses are small DNA viruses whose biological cycle is associated with the terminal differentiation of the keratinocytes of stratified squamous epithelia. The regulatory and nonstructural genes are expressed in the basal layer of stratified epithelia, but the DNA replication, the synthesis of structural proteins and the capsid assembly take place in the superficial layers, in other words, in the keratinocytes undergoing their process of terminal differentiation. The HPV subtypes 16 and 18 are found in more than 90% of uterine cervical cancers and it is accepted that they are involved in the causes of this cancer (zur Hausen, H., J. Natl. Cancer Inst., 92, 690-698, 2000). Uterine cervical cancer represents a major public health problem, which has led to considerable studies aimed at developing prophylactic vaccines (Plummer et al., Virus Res., 89, 285-293, 2002). However, the development of these vaccines has been slowed by the absence of a cell culture method that provides the effective replication and the production of virions.

There remains therefore a need for a method for providing the complete replication of certain pathogenic viruses, in particular enveloped DNA viruses such as, for example, MDV and FPV.

In the knowledge that specific keratinocyte proteins are essential for viral replication, attempts have been made to culture keratinocytes with the aim of providing the production of complete attenuated viruses:

While human keratinocytes can be cultured (Rheinwald et al., Cell, 6, 331-343, 1975), their differentiation state in culture is incomplete. Meyers et al., J. Virol., 71, 7381-7386, 1997, describes the synthesis of infectious HPV virions. Keratinocytes are cultured on 3T3 cells treated with mitomycin in a culture medium called E medium, which is a chicken serum-free synthetic medium.

However, HPV is different from MPV and the method of synthesis of HPV virions described in this document does not make it possible to produce Marek's disease virions.

Document EP-0 748 867 describes cultures of Marek's disease virus serotype 1 on a continuous cell line, the QT35 line. The infected cells are used for the preparation of a vaccine and not for an isolated virion, because this virus is strongly associated with the cell. It is produced with an incomplete envelope and it cannot be isolated while at the same time remaining infectious.

Document EP-0 770 677 describes the propagation of Marek's disease virus serotype 2 on chicken cell lines. The virions obtained are dependent on the cell culture.

Document EP-1 149 899 describes a method of culturing avian ES cells. The culture medium preferably contains a layer of feeder cells, such as STO cells, which are mouse embryonic fibroblasts, inactivated by treatment with mitomycin or by irradiation. It also contains chicken serum.

Document EP-0 779 359 describes a method of culturing avian cells. The culture medium contains chicken serum. The culture is on a support of STO (fibroblast) or SL-10 cells.

It therefore appears that none of the keratinocyte cultures make it possible to offer conditions for providing complete viral replication, in particular envelope DNA viruses such as MDV.

Furthermore, while virtually all human and animal cell types can be cultured successfully in the presence of bovine serum (reference may, for example, be made to Dorange et al., J. Virol., 76, 1959-1970, 2002), chicken keratinocytes do not multiply under these conditions.

The objective of the present invention was to develop conditions for culturing keratinocytes, in particular avian keratinocytes, and more particularly chicken keratinocytes, such as the cells conserve all the differentiation properties that they possess in vivo.

Since the replication cycle of viruses that infect highly differentiated cells (hepatocytes, enterocytes, neuronal cells or keratinocytes) is generally linked to the differentiation program of its host cell (Calnek et al., J. Natl. Cancer Inst., 45, 341-351, 1970; Calnek et al., Avian Dis., 14, 219-233, 1970; Schmitt et al., J. Virol., 70, 1912-1922, 1996), one may expect that cultures of completely differentiated keratinocytes will make it possible to produce complete viral replication and therefore virions devoid of cells.

A subject of the invention is a culture medium for epidermal cells, in particular for fowl epidermal cells, comprising:
(i) chicken serum, and
(ii) a culture support comprising fibroblasts inactivated by antimitotic treatment.

A subject of the invention is also a keratinocyte culture containing a culture medium that comprises chicken serum and a culture support comprising inactivated mammalian cells, preferably inactivated fibroblasts.

In addition, the culture medium of the invention comprises, in a known manner, one or more additives that can be selected from inorganic salts, vitamins, hormones and growth factors or any other additive normally used in cell culture media. Among the additives that can be used in the culture medium of the invention, mention may in particular be made of: inorganic salts, amino acids, vitamins, fatty acids, glucose, a buffer, phenol red, EGF (epidermal growth factor), $T_3$, hydrocortisone, insulin, cholera toxin, transferrin, adenine, etc.

The fibroblasts used as a culture support are advantageously 3T3 cells, and even more advantageously the 3T3-J2 subclone. The origin of the 3T3 line is described in Todaro, G., J. et al., J. Cell Biol., 17, 299-313, 1963. The 3T3 cell line is registered in the ATCC collection under the number CCL92. The 3T3 cells are advantageously used in the invention in the form of a monolayer of cells that are inactivated by antimitotic treatment. Any treatment known for its antimitotic effect can be used. This treatment can consist of treatment with an antibiotic such as mitomycin C, or lethal radiation with gamma rays.

In the culture medium of the invention, the chicken serum is advantageously present in a proportion by weight relative to the total weight of the culture medium ranging from 0.5 to 50%, and preferably from 1 to 40%, advantageously from 2 to 30%.

Advantageously, the growth medium for the cell culture contains at least one, and advantageously several, of the following additives: cholera toxin, transferrin, adenine, EGF, hormones such as $T_3$, hydrocortisone, bovine insulin.

The present invention also relates to a method of culturing keratinocytes, and more particularly avian keratinocytes, said method comprising the steps consisting in:
(i) preparing a suspension of epidermal cells or keratinocytes;
(ii) inoculating said cells onto a cellular support consisting of 3T3 cells in a culture medium comprising chicken serum as described above;
(iii) incubating said epidermal cells on their cellular support.

The suspension of epidermal cells, or keratinocytes, can be obtained, in a known manner, by enzymatic digestion of an epidermis. Such a digestion can be carried out by treatment with a proteolytic enzyme, for instance by treatment with trypsin, with dispase or with thermolysine. It is also possible to envision treating the epidermis by chemical treatment, for instance a treatment with EDTA (ethylenediaminetetra-acetate).

The incubation conditions are those usually applied to a cell culture, i.e. a temperature of approximately 37° C. in 5 to 10% $CO_2$ and 100% humidity.

After incubation, when the cell density is sufficient, the cells obtained under these conditions can be transferred onto a new cellular support and again cultured under the conditions described above. When, at the end of step (iii), the cells derived from the culture are recovered, a further culture cycle is applied to them according to steps (ii) and (iii) of the method of the invention. It is possible to envision up to 30 successive cell multiplication cycles according to the method described above. The doubling time for the cell population is approximately 12 to 16 hours during the first ten cell multiplication cycles, and then it gradually increases during the subsequent cycles. For example, by starting with $10^6$ cells inoculated at the beginning, it is possible to obtain approximately $10^{12}$ cells, i.e. an expansion factor of approximately $10^6$.

The cells obtained after one or more culture cycles can also be conserved in frozen form with a view to their subsequent use. The cell cultures comprising a support of 3T3 cells, a culture medium comprising chicken serum and keratinocytes constitute another subject of the invention.

Surprisingly, it has been possible to demonstrate that the method of culturing according to the invention makes it possible to conserve in the keratinocytes derived from the cell culture all their differentiation characteristics:

Avian epidermis is a stratified squamous epithelium rich in lipids and in alpha- and beta-keratin filaments. The cells of the bottom layer lie on a basal membrane composed of proteins, some of which, such as laminin 5, are specific products of the keratinocytes. The basal layer contains the keratinocyte stem cells that synthesize specific markers: p63. The cohesion of the epidermis is provided by inter-keratinocyte linkages such as desmosomes and gap junctions containing, respectively, the plakoglobin and connexin 31 proteins. In the superficial layers of the epidermis, the keratinocytes undergo a process of terminal differentiation during which they synthesize 14-3-3 sigma and form a cornified envelope that remains insoluble after boiling in detergents and reducing agents. This envelope contains specific proteins such as periplakin.

By means of the method of culture of the invention, the chicken keratinocytes in culture synthesize lipids whose composition is similar to that of avian epidermis, alpha- and beta-keratin filaments, desmosomes, and the p63, 14-3-3 sigma, plakoglobin, connexin 31 and periplakin proteins. Finally, the chicken keratinocytes form, in culture, stratified colonies in the superficial layers of which the cells synthesize a cornified envelope that is insoluble in detergents and reducing agents. Consequently, in the culture system according to the invention, the keratinocytes maintain all the properties that they possess in vivo.

The possibility of obtaining cultures of keratinocytes whose differentiation properties are conserved makes it possible to envision propagating viruses under complete viral replication conditions. In the case of MDV, for example, chicken keratinocytes constitute the only cell type that can provide complete replication of the virus and the production of virions surrounded by a whole envelope. Due to the cytolytic properties of this virus, it is released from the infected cell (Biggs, P. M., Marek's disease, publisher Springer-Verlag, 1-24, 2001) and it can therefore be readily extracted from the culture medium. Furthermore, these cells produce very large amounts of virus, which facilitates the large scale production of these viruses.

Consequently, a subject of the invention is a method of propagating a virus in vitro, this method being characterized in that it comprises the steps consisting in:
(i) infecting keratinocytes with the strain of the virus;
(ii) placing the infected keratinocytes in culture according to the method of culture described above;
(iii) extracting the virions produced in step (ii).

The method of the invention makes it possible to prepare acellular viral particles that can be lyophilized after extraction and therefore allow them to be conserved and stored under more favorable conditions than the infected cell suspensions of the prior art. The virus attenuated by several culture cycles is nevertheless produced in the form of complete virions. This new characteristic makes it possible to envision preparing vaccines that are more effective, providing better immunization than those of the prior art. Preferably, the virus propagation method is carried by performing from 10 to 400 culture cycles, advantageously from 40 to 100 culture cycles. The live, attenuated, enveloped DNA virions derived from the method described above constitute another subject of the invention.

A subject of the invention is also a method of preparing a vaccine, this method being characterized in that it contains the steps consisting in propagating the virus according to the method described above, and then in introducing the virion into a pharmaceutically acceptable carrier, in particular a vaccine carrier. It is advantageously envisioned that the virion is lyophilized and stored before being introduced into the pharmaceutically acceptable carrier. In particular, the vaccine can be transported at ambient temperature. The vaccine carrier can contain, in a known manner, the vaccine adjuvants usually employed.

The method of the invention applies more particularly to the production of vaccines from enveloped DNA viruses for which it was not known, up until now, how to produce acellular vaccines. Among enveloped DNA viruses, mention may in particular be made of the MDV and FPV viruses.

A subject of the present invention is therefore also a live attenuated vaccine comprising a virion obtained from an enveloped DNA virus. Conventionally, such a vaccine comprises a vaccine support in the form of an aqueous solution preferably comprising one or more vaccine adjuvants. Such a vaccine is generally marketed in the form of an immunization kit comprising, firstly, the lyophilized virion and, secondly, the immunization support, each one being packaged in a separate compartment, the two components being mixed extemporaneously with a view to administering them orally or by injection, or via the in ovo route.

It is also possible to envision that the vaccines of the invention can be administered via the respiratory pathway; in this case, they are prepared in the form of an aqueous solution or of an aerosol.

The possibility of culturing keratinocytes makes it possible to develop attenuated viral strains capable of replication in keratinocytes. In the case of the MDV virus, responsible for Marek's disease, after administration of this vaccine to fowl from a poultry farm, these virions would be present in the squamae and therefore capable of infecting and protecting an entire poultry farm. A subject of the invention is also the use of an attenuated virion, for preparing a medicinal product for use in the prevention or treatment of Marek's disease.

The method of culturing keratinocytes of the invention finds other applications in the research field:

The culturing of keratinocytes should make it possible to identify the mechanism of penetration of a virus into this cell type, and in particular to identify the viral envelope proteins required for this penetration. These proteins may subsequently be used in recombinant form for the immunization of animals. In the case of Marek's disease, the complete nucleotide sequence of the virus responsible for this disease is known. The selection of mutant viruses incapable of infecting keratinocytes will make it possible to find the corresponding mutations and therefore the proteins responsible for the penetration into keratinocytes.

The present invention will be subsequently described further and illustrated by examples, which are provided only by way of illustration of the invention and should not be considered as limiting the latter:

EXAMPLE 1

Multiplication of Chicken Keratinocytes with 3T3-J2 Support Cells in the Presence of 10% Chicken Serum 1.1 Introduction The growth of the chicken fibroblasts is not eliminated effectively by the monolayer of 3T3 cells and the cultures prepared from full-thickness chicken skin are rapidly invaded by the fibroblasts. The epidermis was therefore separated from the dermis by treatment with thermolysin, before carrying out the disaggregation of the epidermis. Initially, the medium had been supplemented with fetal calf serum, but this serum does not allow multiplication of the chicken keratinocytes. Substitution of the bovine serum with chicken serum allows the development of cell colonies.

1.2 Materials and Methods 1.2.1 Biological Material

Newborn chicks (*Gallus gallus*) are obtained from fertilized eggs incubated for 20-21 days at 37.8° C. at a high humidity level. To prepare the primary cultures of epidermal cells, the newborn chicks are anesthetized by intraperitoneal injection of tribromoethanol.

Murine 3T3-J2 cells: The origin of the 3T3 line is described in Todaro, G., J. et al ., J. Cell Biol., 17, 299-313, 1963. Original Swiss 3T3 cells obtained from the ATCC (No. CCL92) are inoculated at low density into 96-well plates (at a rate of one cell per three wells). After approximately two weeks of culture, some wells contain visible cell colonies. These cultures are clonal since they are derived from a single cell, each one therefore constitutes a 3T3 subclone. Each colony is transferred separately into a culture dish 100 mm in diameter. When the number of cells is sufficient, the cells are detached by trypsinization. Half of each subclone is frozen in liquid nitrogen; the other half is treated with mitomycin C or with gamma rays. Chicken keratinocytes are inoculated onto each treated subclone at densities of $10^2$ to $10^6$ cells per $1.5 \times 10^6$ 3T3 per 100 mm diameter dish. After 7-14 days of culture, these cells are fixed and stained with rhodamine B. The 3T3 subclone, called 3T3-J2, on which there are the largest number of keratinocyte colonies of the largest size is considered to be optimal; from now on, it will be used for culturing the chicken keratinocytes.

Human epidermal keratinocytes originating from newborn foreskin (prepared according to the method described in Rheinwald et al., Cell, 6, 331-343, 1975).

1.2.2 Methods

Cell Culture (Method 1):

The skin from the feet or from the body is removed; it is washed several times in phosphate buffered saline (PBS), and the epidermis is then separated from the dermis by enzymatic treatment with 0.5 mg/ml of thermolysin (Sigma) in a Hepes buffered solution (HBS) either for 45 minutes at 37° C. or overnight at 4° C. The epidermis is then removed, cut up into thin slices and disaggregated by incubation in the presence of trypsin (0.25%) and EDTA (0.02%) for two times 30 minutes at 37° C. with agitation in a trypsinization flask. The cell suspension is centrifuged at 800 g for 5 minutes. The cell pellet is taken up in culture medium and the cells are inoculated into Petri dishes coated with a monolayer of murine 3T3 cells ($2.3 \times 10^4$ cells/cm$^2$) treated beforehand with mitomycin C (4 µg/ml). The dishes are subsequently placed in an incubator at 37° C. in 7.5% $CO_2$ and 100% humidity. The culture medium consists of a 1/1 DMEM/F12 mixture (Invitrogen) supplemented with 10% chicken serum (Invitrogen). The following additives are also present in the medium: 0.4 µg/ml hydrocortisone (Calbiochem), 5 µg/ml of bovine insulin (Sigma), $2 \times 10^{-9}$ M of 3,3',5-triiodo-L-thyronine (T3, Sigma), $10^{-10}$ M of cholera toxin (ICN) and $1.8 \times 10^{-4}$ M of adenine (Calbiochem). Recombinant human epidermal growth factor (EGF) is added at a concentration of 10 ng/ml at the first change of medium. In certain cases, fibroblast colonies develop despite the elimination of the dermis, but they can be eliminated by briefly treating the cultures with PBS without Ca++ and without Mg++, or with 0.02% EDTA; further 3T3 support cells are then added and the culture is continued. The primary cultures are transferred 7 to 19 days after inoculation according to the inoculation density. Secondary cultures are then obtained. The cells are frozen after the first passage, in medium containing 10% dimethyl sulfoxide (DMSO). The freezing is carried out at a rate of $1-3 \times 10^6$ cells/ml in the culture medium described above. The frozen cells can be kept indefinitely in liquid nitrogen.

The human epidermal keratinocytes are placed in culture as described for the chicken cells, except that fetal calf serum is used in place of the chicken serum.

Cell culture (Method 2): Culturing of Chicken Keratinocytes at the Liquid/Air Interface This method is based on the article J. Y. Yi et al., Arch. Dermatol. Res., 2001, 293, 356-362. Its aim is to obtain a more complete terminal differentiation. The 3T3 cells treated or not treated with mitomycin are mixed with a collagen type I matrix ($3 \times 10^5$ cells/ml) according to the supplier's instructions (Nitta gelatin, Tokyo), and 200 micro liters of this mixture are inoculated onto polycarbonate filters (Millicell-pc Millipore, Bedford, Mass.). The keratinocytes are inoculated onto the collagen matrix and cultured while immersed for 5-7 days in the usual culture medium (DMEM/F12+chicken serum+additives). The filter is subsequently placed at the medium/air interface and the culture is continued for 14 days.

Phase Contrast Microscopy

A Nikon microscope equipped with a Nikon Coolpix digital camera was used.

Staining of Lipid Droplets with Oil Red O

Cells inoculated onto glass coverslips are fixed in cold PBS containing. 3.7% formaldehyde for 15 minutes at ambient temperature, and then incubated for an additional hour with a fresh fixing solution. The glass coverslips are washed with distilled water and air-dried. The lipid droplets are stained with a solution containing 0.3% of Oil Red O (Sigma) and 60% of isopropanol for one hour. At the end of the incubation, the glass coverslips are washed in distilled water and incubated for 5 minutes in PBS containing Hoechst 33258 reagent (1 µg/ml) and 0.1% of the product sold by the company Sigma under the trade name Igepal. The glass coverslips are washed once in PBS/Igepal and once in water, and are mounted on a slide in product sold by the company Calbiochem under the tradename Mowiol containing 2.5% of DABCO (1,4-diazobicyclo(2.2.2)octane).

1.3 Results

Figure 1:
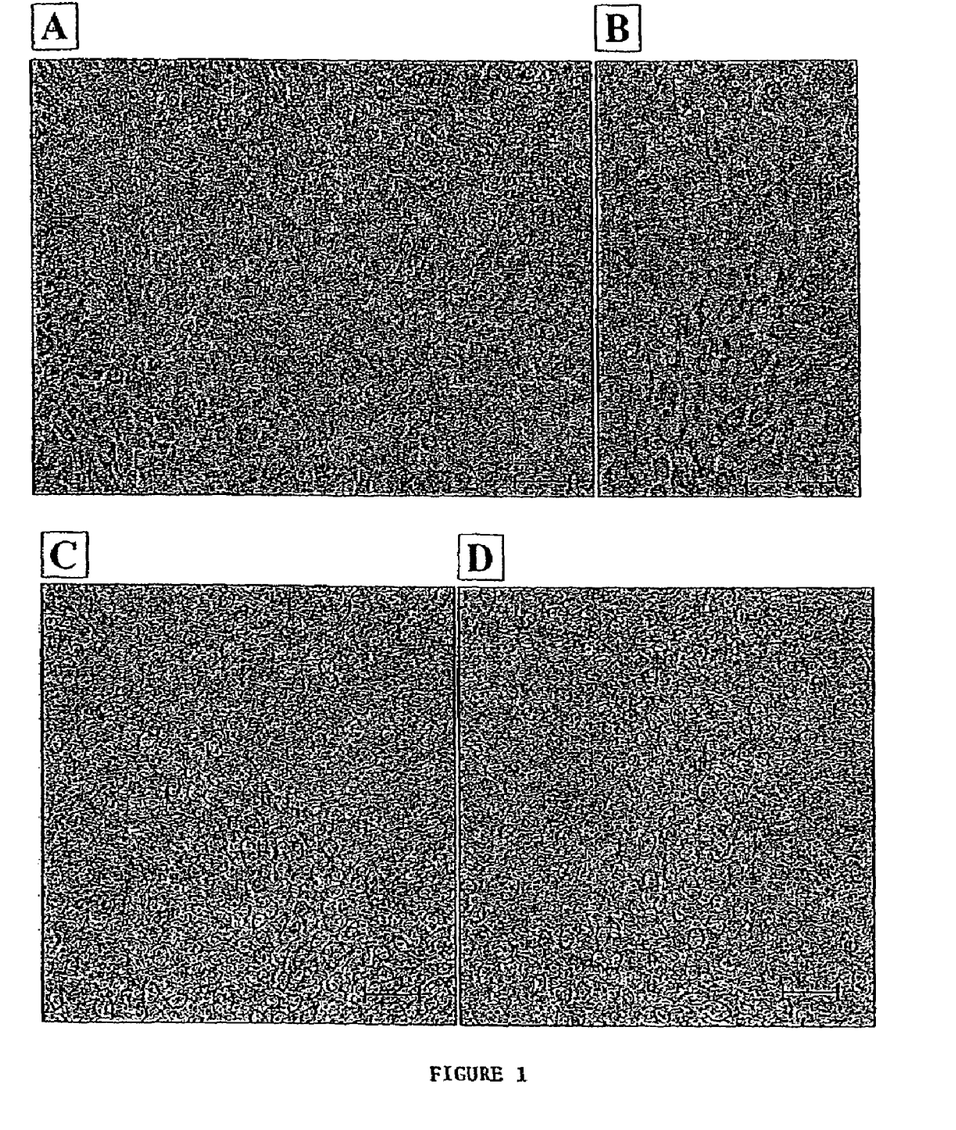
FIG. 1 represents phase microscope photographs which illustrate the growth of the chicken and human epidermal cells: (A) $10^5$ chicken epidermal cells in their $3^{rd}$ passage are placed in culture in a medium containing 10% chicken serum; (B) the same culture as in (A), taken with a higher magnification; (C) $7.8 \times 10^5$ human keratinocytes (YF23) are placed in culture in a medium containing 10% fetal calf serum; (D) the human keratinocytes (YF23) are placed in culture in a medium containing 10% chicken serum; each scale bar corresponds to 50 µm.

Round cells attached to the 3T3 cells are visible after a few hours of inoculation, but the colonies that organize clearly into a typical epithelial unit become visible after 5-6 days of inoculation, when the cells have established a contact with the plastic. The colonies displace the monolayer of 3T3 cells around them, as do the colonies formed by the human keratinocytes. What appears to be most noticeable is that almost all the cells contain a single large droplet and sometimes several small ones, probably composed of lipids (FIGS. 1A and 1B). By virtue of their epidermal origin and their ability to form a stratified squamous epithelium, and given that avian keratinocytes are known to contain lipid droplets, it is concluded that the colonies are composed of keratinocytes.

The human keratinocytes inoculated at a density of 12 000 cells/cm$^2$ in a medium supplemented with 10% chicken serum multiply as rapidly as they do in fetal calf serum. They never develop lipid droplets even after 12 days in the presence of 10% chicken serum (FIGS. 1C and D). It is concluded from this that the formation of lipid droplets is an intrinsic property of chicken keratinocytes and is not induced in keratinocytes of other species by chicken serum.

Figure 2:
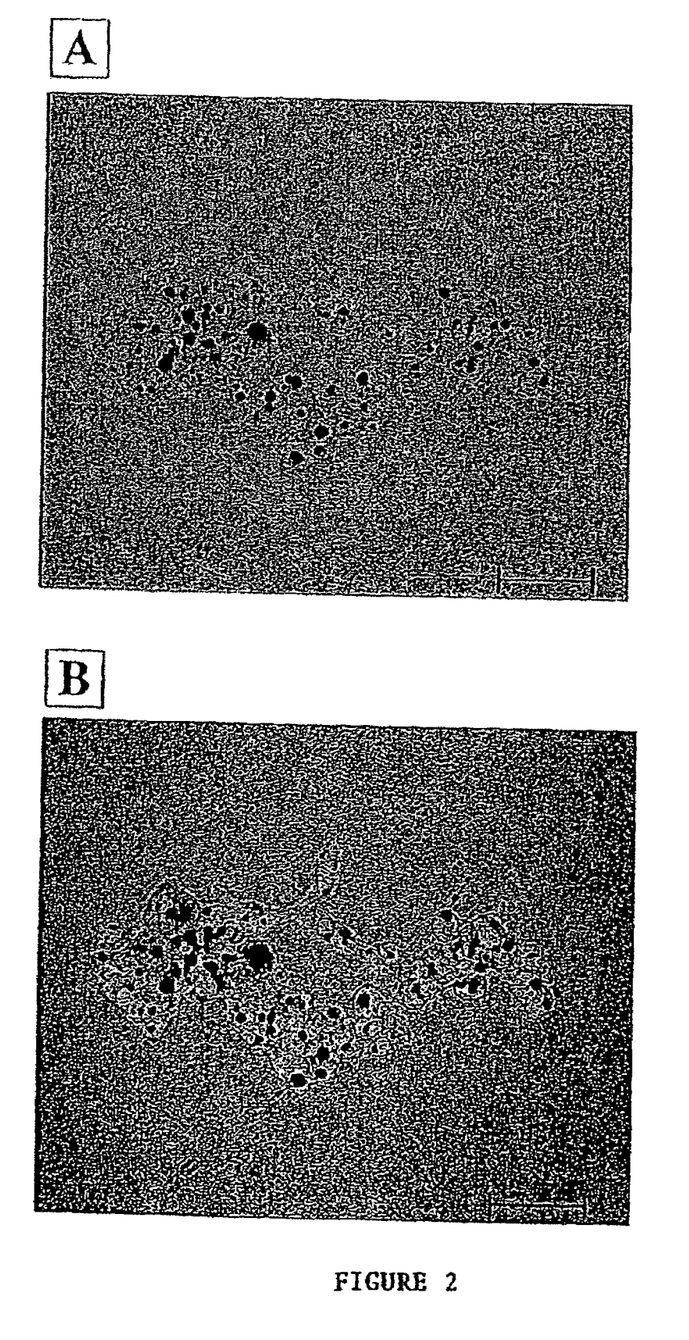
FIG. 2 illustrates the accumulation of cytoplasmic lipids by the keratinocytes in culture after labeling with Oil Red-O and staining with the Hoechst 33258 reagent; (A) phase microscopy with a yellow filter; (B) photograph of the same field taken both under phase contrast and under fluorescence and printed in black and white; the arrows show the nuclei stained with the Hoechst 33258 reagent (white), the scale corresponds to 25 µm.

The staining of the fixed cells with the Oil Red-O product, which is specific for neutral lipids, shows that the refringent droplets contain neutral lipids (FIG. 2A); counter staining with the Hoechst 33258 reagent demonstrates that most of the lipid droplets in the cells are perinuclear (FIG. 2B).

In three independent experiments, it was demonstrated that approximately 500 colonies were formed from 5×10$^5$ disaggregated epidermal cells. This corresponds to a colony-forming efficiency of 10$^{-3}$. The seeding efficiency for the chicken keratinocytes taken directly from epidermis is therefore significantly lower than that of the human keratinocytes, which has been reported to be of the order of 1 to 10% but is in general close to 1%. Unlike the human keratinocytes, which attain very high colony-forming efficiencies in the subsequent passages, the seeding efficiency for the chicken keratinocytes never exceeds a few percent.

The doubling time of the chicken keratinocytes is measured in the secondary culture by counting the number of cells in 15 colonies, every 24 hours, from the 1$^{st}$ day to the 4$^{th}$ day after inoculation. The chicken keratinocytes can be readily distinguished from the neighbouring 3T3 cells given that they contain a solitary lipid droplet. When the colonies with the highest growth rate are taken into consideration, a doubling time of 16.8 hours is obtained. The doubling time decreases in the course of the subsequent passages and the chicken keratinocytes cannot be placed in culture beyond the 20$^{th}$ subculture.

The size of the chicken keratinocytes is measured by introducing a suspension of cells into a hematocytometer, photographing the cells and measuring their diameter. The keratinocytes have a typical diameter of 10 μm, and are therefore smaller than the human keratinocytes, the most common diameter of which is 12 μm. This difference can be explained by the fact that the size of the chicken genome is only a third of that of a human (1.25 pg versus 3.5 pg/haploid genome). Chicken fibroblasts, with a typical diameter of 12 μm, are also smaller than human fibroblasts, the most common diameter of which is 15.6 μm.

EXAMPLE 2

Role of Chicken Serum in the Chicken Keratinocyte Multiplication Process 2.1 Introduction Fetal calf serum does not allow multiplication of the chicken keratinocytes, either because it contains a multiplication inhibitor, or because it lacks a growth-promoting factor.

In order to distinguish between these alternatives, the chicken keratinocytes are cultured for 10 days either in the presence of 10% fetal calf serum supplemented with increasing concentrations of chicken serum, or in the presence of 10% chicken serum supplemented with increasing concentrations of fetal calf serum. At the end of the experiment, the cells are fixed and stained with rhodamine B.

2.2 Materials and Methods 2.2.1 Materials

The biological material used is that described in Example 1.

2.2.2 Methods

The cell culture protocol is used according to that described in Example 1.

Staining with Rhodamine B

The cultures are washed twice with PBS and fixed in PBS containing 10% glutaraldehyde, for 15 minutes at ambient temperature. The cells are then stained with 1% rhodamine B in water for 15 minutes at ambient temperature with gentle agitation. The cultures are washed in water and are subsequently air-dried.

2.3 Results

Figure 3:
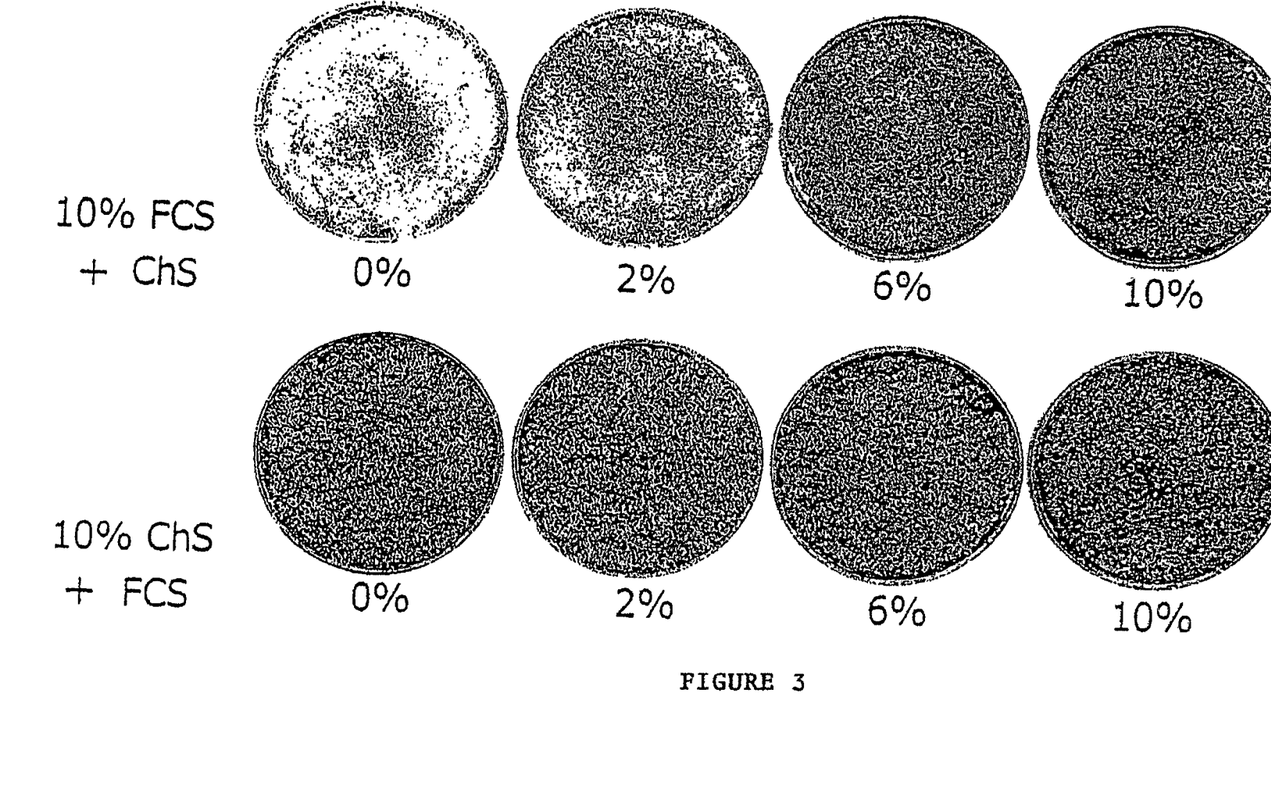
FIG. 3 illustrates the effect of chicken serum on the multiplication of chicken keratinocytes; $5 \times 10^4$ cells are placed in culture in a mixture of chicken serum (ChS) and of fetal calf serum (FCS), and are then fixed and stained with rhodamine B; in one case, the percentage of FCS in the culture medium is fixed at 10% and the percentage of ChS is variable. In the other case, the percentage of ChS in the culture medium is fixed at 10% and the percentage of FCS is variable.

In FIG. 3, it appears clearly that the chicken serum allows multiplication of the keratinocytes and that this faculty depends on the dose of chicken serum, when it is added to 10% fetal calf serum. The growth-promoting activity of 10% chicken serum is not affected by the addition of increasing amounts of fetal calf serum. It is concluded therefrom that the chicken serum contains a factor necessary for the multiplication of chicken keratinocytes, this factor being absent from fetal calf serum.

Figure 4:
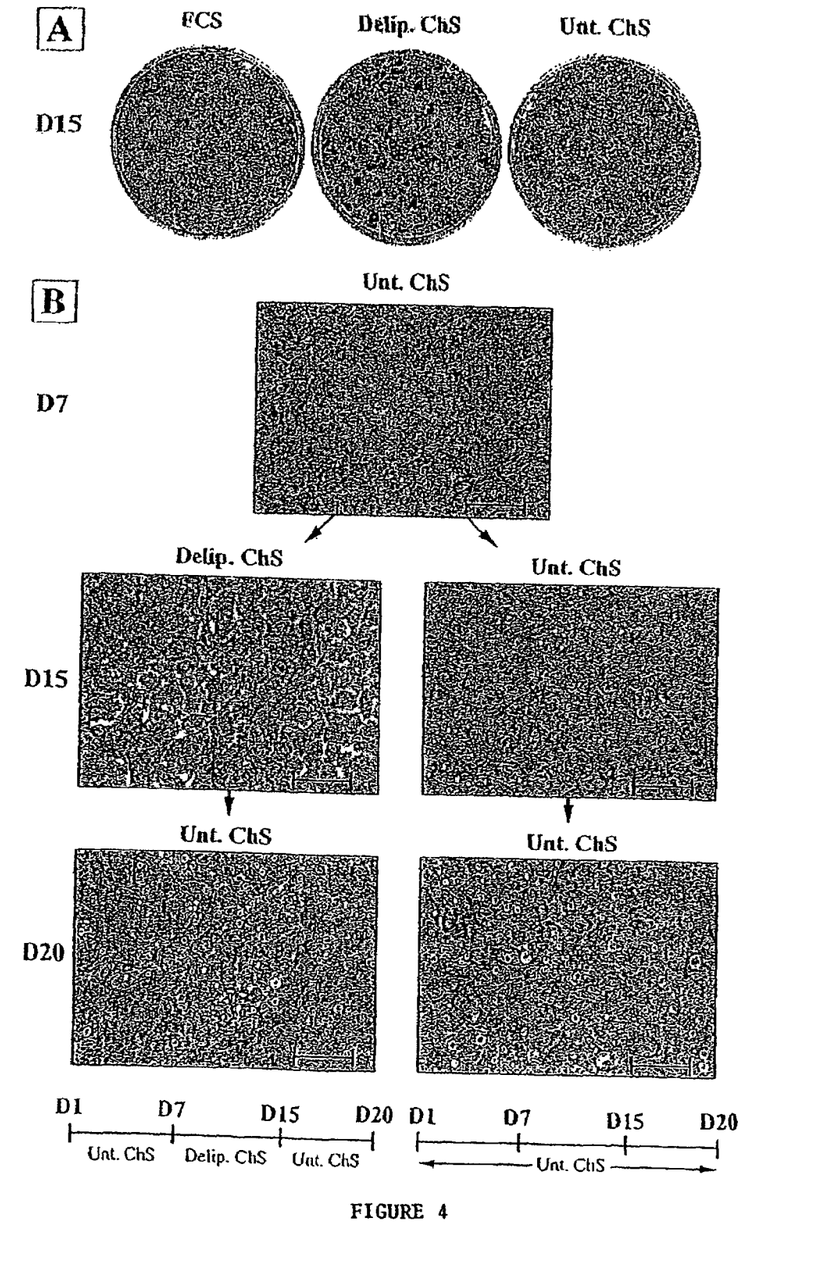
FIG. 4 illustrates the fact that delipidizing the chicken serum does not affect the multiplication of the chicken keratinocytes; chicken keratinocytes, with a density of 3500 cells/$cm^2$, are inoculated and placed in culture in 10% chicken serum for 7 days; in some dishes, the serum supplement is replaced, either with fetal calf serum (FCS), or with delipidized chicken serum (Delip. ChS), whereas the cells in the other dishes are maintained in untreated chicken serum (Unt. ChS); D1: $1^{st}$ day, D7: $7^{th}$ day, D15: $15^{th}$ day, D20: $20^{th}$ day; (A) the cultures are fixed 15 days after inoculation and stained with rhodamine B; the arrows indicate small droplets observed in delipidized serum.

Given that chicken keratinocytes contain lipids, it could be assumed that the growth-promoting activity of chicken serum is linked to the absorption of lipids in the serum. The experiment illustrated by FIG. 4A shows that chicken serum lacking lipids due to the action of solvents retains its ability to promote chicken keratinocyte multiplication. Consequently, the growth-promoting activity is not due to a lipid. The cells that multiply, in particular around the colonies, retain the lipids when they grow in delipidized serum and are therefore capable of synthesizing lipids (FIG. 4B).

EXAMPLE 3

The Chicken Keratinocytes in Culture Synthesize Alpha-keratins 3.1 Introduction

One of the properties of epidermal cells is their ability to synthesize keratinocytes in abundance. Chicken keratinocytes are placed in culture on glass coverslips for two days and are fixed. The cells are then incubated in the presence of an anti-alpha-pankeratin antibody and examined by indirect fluorescence microscopy.

The keratins of the chicken epidermal cells in culture were analyzed by Western blotting immunodetection. The keratins are extracted from confluent cultures, separated by one-dimensional gel electrophoresis, transferred onto nitrocellulose, and stained using an anti-alpha-pankeratin antibody.

3.1 Materials and Methods 3.1.1 Materials

The biological material is that described in Example 1.

3.2.1 Methods

Indirect Immunofluorescence Staining

The cells are inoculated onto glass coverslips. The following day, the cells are washed twice in PBS, and then fixed in a 1:1 mixture of acetone:methanol for 20 minutes at −20° C. and air-dried. The glass coverslips are incubated in PBS containing 5% bovine serum albumin (BSA) for 10 minutes at ambient temperature in order to block the nonspecific sites.

For the alpha-keratin staining, the cells are incubated for one hour at ambient temperature in 5% of BSA/PBS containing a mouse monoclonal anti-pankeratin antibody (1:100 dilution, MS-744-A0, NeoMarkers), before being washed 3 times for 5 minutes each time with PBS containing 0.1% of the nonionic detergent Igepal CA 630 (Sigma). The cells are then incubated for one hour at ambient temperature in the presence of 5% BSA/PBS containing goat anti-mouse IgGs conjugated to biotin (1:1000 dilution, Jackson ImmunoResearch). The glass coverslips are washed and incubated for one hour with streptavidin conjugated to cyanin-3 (1:1000 dilution). At the end of the incubation, the glass coverslips are washed for 5 minutes in PBS/Igepal before being incubated for 5 minutes in PBS containing Hoechst 33258 reagent (1 µg/ml) and 0.1% of Igepal. The glass coverslips are washed once in PBS/Igepal and once in water, and are mounted on a slide in Mowiol containing 2.5% of 1,4-diazobicyclo(2.2.2) octane (DABCO).

Extraction of α-keratins and Analysis by Immuno-detection (Western Blotting)

Confluent cultures are washed twice with PBS and ground using a Dounce homogenizer. The cells are homogenized after 20 rotations in a buffer containing 10 mM of Tris-HCl (pH 7.6), 1 mM EDTA and a mixture of protease inhibitors (Roche). The homogenate is centrifuged at 8000 g for 5 minutes at 4° C. and the pellet is washed twice with Tris-EDTA buffer and twice with Tris-EDTA buffer containing 2% of Nonidet P40. The keratins in the final pellet are suspended in a solution containing 2% of SDS and 10 mM of dithiothreitol, at 37° C. for 15 minutes, using an ultrasound device (2×15 seconds). The samples are then heated at 100° C. for 2 minutes and centrifuged for 5 minutes at 8000 g in order to remove the insoluble residues.

The α-keratins are separated by electrophoresis on a denaturing 8% polyacrylamide gel (proportion by weight of acrylamide:bisacrylamide, 29:1) and electroeluted onto nitrocellulose. The membrane is treated overnight at 4° C. in PBS containing 5% of dried skimmed milk and 0.1% of Tween 20 (PBST). The alpha-keratins are stained with an anti-pankeratin antibody consisting of a mixture of two monoclonal antibodies, one being directed against type I keratins and the other being directed against type II keratins (PRO61835, Research Diagnostics Inc). The antibody is used at a dilution of 1:500, and the membrane is washed with PBST before being incubated with a 1:2000 dilution of donkey anti-mouse IgGs conjugated to horseradish peroxidase (Amersham). The antibody incubations last one hour at ambient temperature. The bands corresponding to keratin are visualized by chemiluminescence (ECL+kit, Amersham).

3.3 Results

Figure 5:
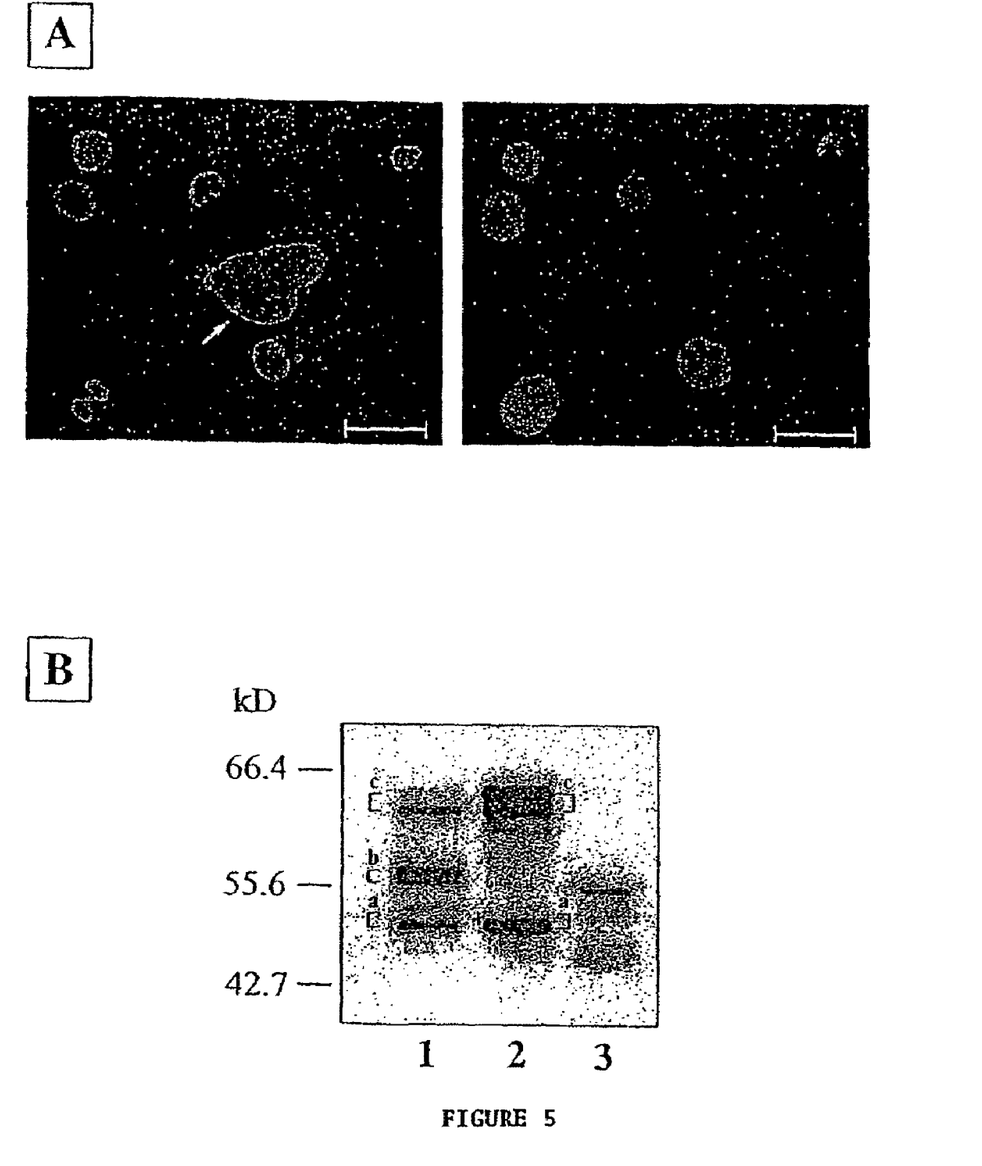
FIG. 5 illustrates the demonstration of keratins in the chicken keratinocytes in culture; (A) the cells are labeled with an anti-pankeratin antibody; the arrow indicates a 3T3 cell, which is multinuclear and is not labeled with the antibody; the scale corresponds to 25 µm; (B) immunoblot labeled with another anti-pankeratin antibody; lane (1) corresponds to the chicken keratinocytes in culture; lane (2) corresponds to chicken epidermis and lane (3) corresponds to chicken intestine; the two doublets (a and c) coincide with the corresponding doublets in the chicken epidermis.

All the chicken keratinocytes in culture are strongly labeled, but the 3T3 cells are not labeled (FIG. 5A). No labeling is observed when the specific antibody is omitted.

The results from immunodetection are illustrated in FIG. 5B. The proteins stained with the antibody are separated into three major doublets (a-c), the respective molecular weights of which are approximately 50, 57 and 63 kD. The doublets a and c are also present in chicken skin, but the doublet b is not. The general profile of the keratins extracted from chicken intestine, a non-keratinizing epithelium, does not coincide with the epidermal cells, nor with the epidermis. Given that the cells in culture contain two keratin doublets the molecular weights of which coincide with those of epidermal keratins, the applicant concludes from this that the cells in culture synthesize epidermal keratins. The two high molecular weight keratins (doublet c in FIG. 5B) are particularly relevant given that high molecular weight keratins are considered to be specific for the outer layers of stratified squamous epithelia. Four α-keratins are further characterized (see below).

EXAMPLE 4

The Chicken Keratinocytes form Cornified Envelopes in Culture 4.1 Introduction

One of the distinctive properties of mammalian epidermal keratinocytes is their ability to follow the terminal differentiation process, in which their nucleus is destroyed and during which they develop a cornified cellular envelope that is insoluble in the presence of sodium dodecyl sulfate and of 2-mercapto-ethanol.

4.2 Materials and Methods

The biological material and the methods used in this example are those described in Example 1.

4.3 Results

Figure 6:
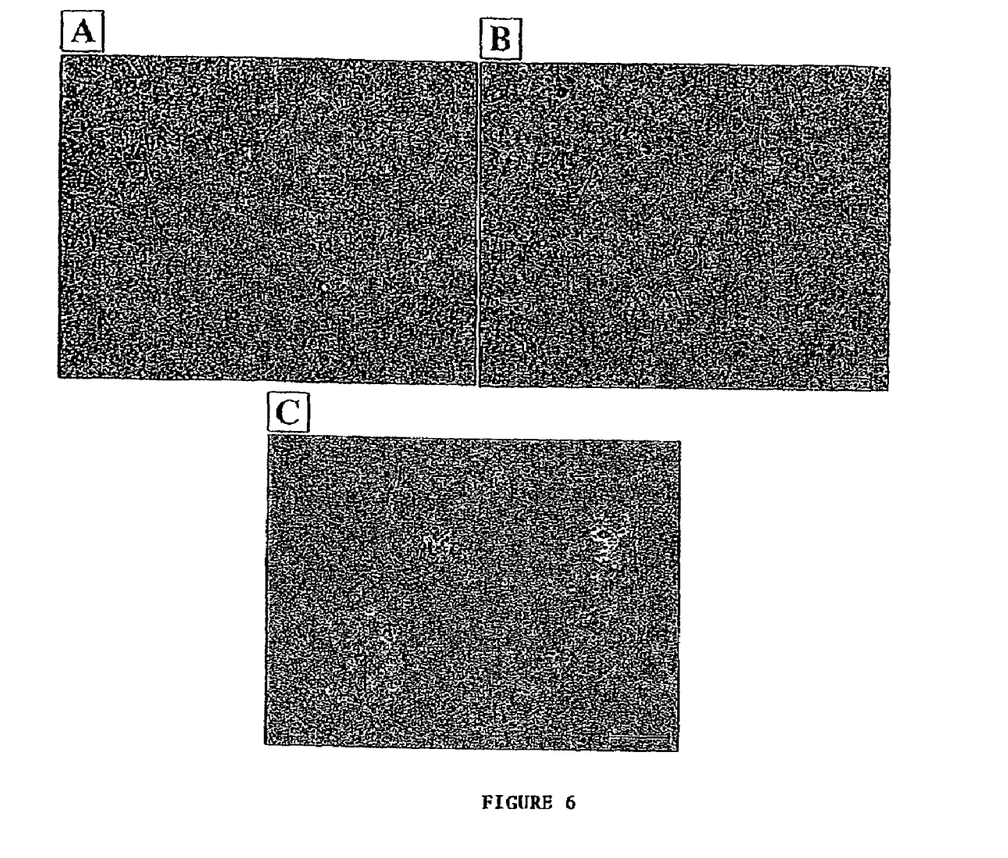
FIG. 6 shows that the chicken keratinocytes form cornified envelopes in culture; the photographs are taken under phase contrast microscopy; (A) basal layer of a 15-day live colony, (B) the same colony taken on a higher focal plane; the dark contours and the angular shape indicate a cornification, (C) after treatment at 100° C. in a solution containing 2% sodium dodecyl sulfate and 2% 2-mercaptoethanol; the scale corresponds to 50 µm.

When the center of the chicken keratinocyte colonies whose size exceeds several hundred cells is observed, it is noted that they almost always contain large cells that each cover several basal cells (FIGS. 6A and B). These squamae are rapidly released into the medium, and they always contain refringent droplets, probably composed of lipids. Chicken squamae are thinner and are approximately twice as large as human squamae (greater length of 100 µm versus 50 µm) (FIG. 6B). When the chicken epidermal colonies are removed and placed in a solution containing 2% of SDS and 2% of 2-mercapto-ethanol and heated to 100° C., most of the cells dissolve, but the cornified envelopes remain insoluble and still retain lipid droplets (FIG. 6C). A large part of the envelopes prepared directly from chicken epidermis also retain lipids after boiling in SDS/2-mercaptoethanol. These lipids can be extracted with methanol/chloroform.

EXAMPLE 5

The chicken Keratinocytes Contain p63

The p63 protein, which is part of the family of the gene encoding the p53 protein, is abundantly present in the basal layer of many epithelia. In human epidermis, p63 is found only in cells having a high proliferative potential. Knockout of the gene encoding p63 results in an absence of any stratified squamous epithelium and p63 is considered to be a marker for keratinocyte stem cells.

In order to determine whether the chicken keratinocytes contain p63, rapidly growing cells are seeded onto glass coverslips and observed the following day by immunofluorescence microscopy, using the monoclonal anti-p63 antibody 4A4.

5.1 Materials and Methods 5.1.1 Materials

The biological material is described in Example 1.

5.1.2 Methods

The cell culture and the indirect immunofluorescence staining technique are those described, respectively, in Examples 1 and 3.

p63 Labeling

The cells are incubated overnight at 4° C. in the presence of an anti-human p63 monoclonal antibody 4A4, diluted to 1:500. The rest of the protocol is identical to that used for the keratin staining, except that the secondary antibody is used at a dilution of 1:200. The cells are photographed using a Nikon E600 fluorescence microscope equipped with a Nikon digital photographic device.

5.2 Results

Figure 7:
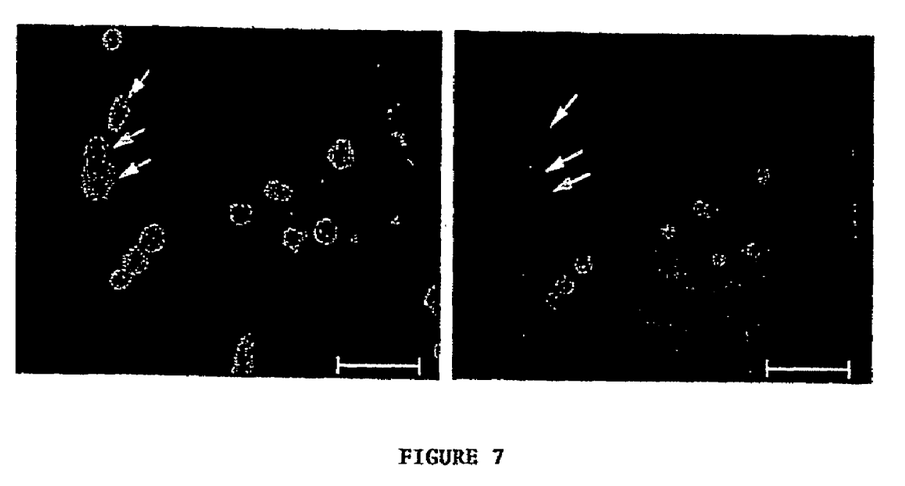
FIG. 7 illustrates p63 labeling by immuno-fluorescence staining using an anti-p63 antibody; the arrows indicate the 3T3 cells that are recognized by means of their large nuclei and their prominent heterochromatin; they are not labeled with the antibodies; the scale corresponds to 25 µm.

All the cells examined exhibit strong nuclear staining for p63. Conversely, the 3T3 cells exhibit either no labeling or sometimes a weak cytoplasmic labeling (FIG. 7).

EXAMPLE 6

Characterization of the Chicken Keratinocytes by Eelectron Microscopy 6.1 Materials and Methods Chicken keratinocyte monolayer cultures are prepared. When the cells are two thirds confluent, the 3T3 cells are removed using EDTA, and the keratinocytes are transferred into small Petri dishes in the absence of 3T3 support cells. The following day, the cells are fixed and treated so as to be observed by electron microscopy.

Electron Microscopy

The cells are washed in 0.1M cacodylate at pH 7.3, fixed for 90 minutes with 5% paraformaldehyde and 5% glutaraldehyde in 0.1M sodium cacodylate at pH 7.2, and observed by conventional electron microscopy. Ultrathin sections, stained with uranyl acetate and lead citrate, are examined at 80 kV using a Jeol JEM-1010 electron microscope (Jeol Ltd, Tokyo, Japan).

6.2 Results

Figure 8:
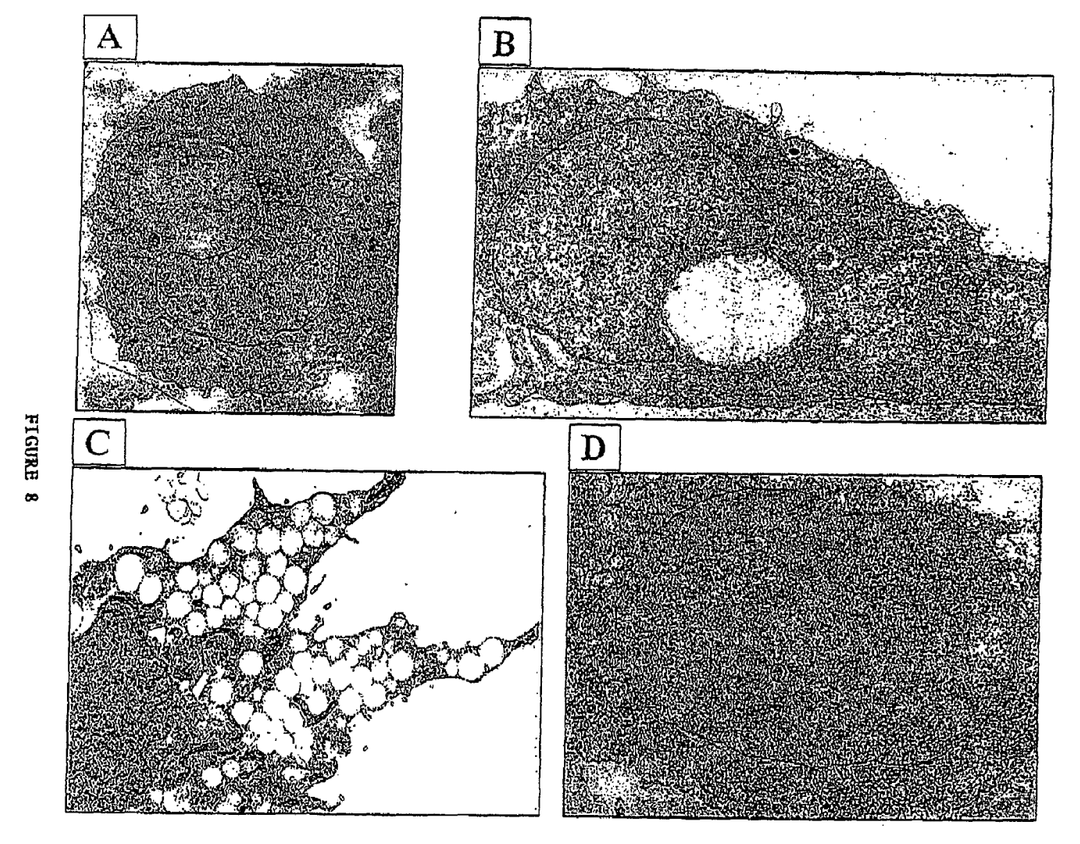
FIG. 8 shows perinuclear and intranuclear lipids; these are electron micrographs; magnification scales: 5000× for A and B, 6000× for C and 4000× for D.
Figure 9:
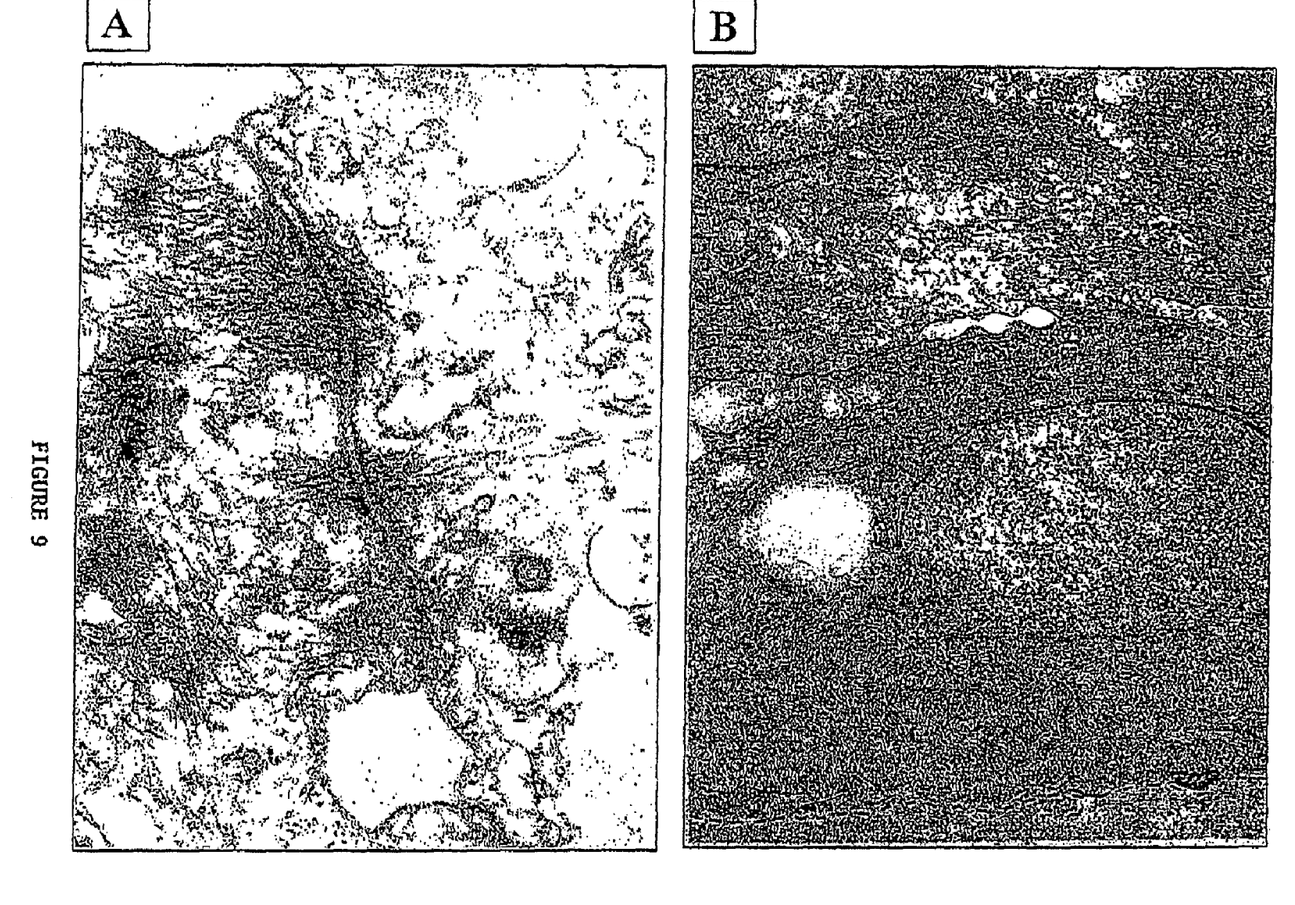
FIG. 9 shows the stratification in the keratinocytes; the desmosomes (in A) and the keratin filaments (in B); these are electron micrographs; magnification scales: 40 000× for A and 8000× for B.

FIG. 8 shows a set of micrographs of cells containing lipid droplets. Two micrographs (A and B) show a typical cell with a single perinuclear lipid droplet that is embedded in the nucleus. Thus, most of the nuclei exhibit a crescent shape. The other two photographs show a cell with multiple small cytoplasmic lipid droplets (C) and another cell with lipid droplets inside the nucleus (D); these two characteristics being commonly present. FIG. 9 shows typical epidermal cell characteristics. Photograph (A) demonstrates the presence of desmosomes. Photograph (B) shows a basal cell and a superbasal cell in which the cytoplasm is filled with tonofilaments (keratin).

EXAMPLE 7

Identification of Specific Keratinocyte Products by Random Sequencing 7.1 Introduction A cDNA library is constructed from confluent chicken keratinocyte cultures. The nucleotide sequence of the 5' end derived from 163 random clones is determined using an automatic sequencer. The GenBank and protein databanks are then used for homology searches with the cDNA sequences.

7.2 Materials and Methods

Construction of the cDNA Library and Nucleotide Sequencing

Total RNA is purified from chicken keratinocytes in culture using the Tripure Isolation Reagent (Roche). The poly(A)$^+$ RNAs are isolated on oligo(dT) cellulose using the Micropoly (A) Purist™ (Ambion) mRNA purification kit. A cDNA library is prepared from 1.7 μg of poly(A)$^+$ RNA using the SuperScript™ Plasmid System (Life Technologies). The first strand synthesis is initiated by means of a primer containing an oligo(dT) sequence followed by a NotI site. A SalI adapter is added at each end of the cDNA after the synthesis of the $2^{nd}$ strand. Digestion with NotI generates a sticky end at the 3' end, while the SalI sticky end remains at the 5' end. The cDNAs are ligated to the plasmid pSport1 cleaved beforehand with SalI and NotI, and introduced by electroporation into electrocompetent *E. Coli* DH10B bacteria (Life Technologies).

The random sequencing of the 5' end of the cDNA clones is carried out using a primer that hybridizes to the plasmid, upstream of the SalI site. To extend the sequence, specific internal primers are used:

for α-keratin 5/6:

SEQ ID NO: 1    5'-AGTGGATTCTATGGACCTGC-3',

SEQ ID NO: 2    5'-AACTGAGCAGCTTGCTGGC-3',

SEQ ID NO: 3    5'-CAGTCCAGGTACGAAGAGC-3'

SEQ ID NO: 4    5'-TAGGATCGGGATATGGAAGC-3';

for α-keratin 15:

SEQ ID NO: 5    5'-GGCTTTGATGCTATCTGTGC-3',

SEQ ID NO: 6    5'-GTGGAGTCTGACATCAACG-3'

SEQ ID NO: 7    5'-AGAACTGAGACGCACGATGC-3';

for β-keratin K:

SEQ ID NO: 8    5'-ACTAGGATGTTACTGCGTGG-3'.

The sequencing is carried out on a GeneAmp 2400 PCR machine (Perkin-Elmer) in the presence of fluorescent dideoxynucleotides. The PCR conditions are 30 cycles at 96° C. for 30 seconds, 50° C. for 15 seconds and 60° C. for 4 minutes. Electrophoresis and detection of fluorescence peaks are carried out on an automatic sequencer (ABI PRISM 310 Genetic Analyzer). The sequence is determined using the SeqEd v1.0.3 program.

7.3 Results 50 clones exhibit no homology with the database sequences. 15 clones exhibit homologies with hypothetical proteins. 86 clones encode universal proteins having known functions. 12 clones encode proteins known to participate in specific keratinocyte functions. The applicant concludes from this that, in the chicken keratinocytes, approximately 40% (65/163) of the mRNAs encode proteins of unknown function and that approximately 12% (12/98) of the mRNAs are specific for this cell type. In total, 7 keratinocyte-specific clones encode keratins (Table III). Clones 6-8 encode the same alpha-keratin, whereas clones 9-11 encode various α-keratins and clone 12 encodes a β-keratin. The entire nucleotide sequence is determined for clones 6 and 9-12.

EXAMPLE 8

Infection of Chicken Keratinocytes in Culture with the Marek's Disease Virus (MDV)

8.1 Materials and Methods

The infected cells, derived from chicken skin primary cells (essentially fibroblasts) or blood lymphocytes infected with MDV-1, are seeded onto chicken keratinocytes in subconfluent culture and incubated for one hour at 37° C. After adsorption, the inoculum is removed by suction and the chicken keratinocyte monolayers are washed three times with a phosphate buffered saline (PBS). The cell culture medium is added and the cells are incubated for one week at 37° C.

The completely enveloped MDV virions are released into the cell culture medium, which can be recovered and lyophilized. For lyophilization, the cell culture medium containing the MDV virions is frozen at −60° C., dried under vacuum at 38° C. for 24 hours, dried for 15 hours at 21° C., and stored at 4° C. under vacuum.

The infected chicken keratinocyte cultures are removed in PBS, or in PBS containing 0.2% EDTA, or in an "SPGA" stabilizing solution consisting of $2.18 \times 10^{-1}$M of sucrose, $7.2 \times 10^{-3}$M of dipotassium phosphate, $3.8 \times 10^{-3}$M of potassium phosphate, $4.9 \times 10^{-3}$M of sodium glutamate and 1% of powdered bovine albumin, or in SPGA containing 0.2% EDTA (SPGA-EDTA), or in SPGA-EDTA with 10% of sorbitol, or in a cell culture medium with 10% sorbitol. The cell suspensions are then ruptured by ultrasound for 2 minutes and centrifuged at 2000 g for 20 minutes, and the supernatants are recovered as cell-free viral preparations. The viruses are extracted from the infected keratinocytes by means of three freezing/thawing cycles, and the supernatant fluids are recovered. The cell-free viruses can be lyophilized as described above.

The invention claimed is:

1. A culture medium comprising a chicken serum and a culture support comprising inactivated 3T3 cells, wherein the 3T3 cells are derived from the 3T3 cells of the cell line registered in the ATCC collection under the number CCL92 by means of a method comprising the steps of inoculation into wells, culture, transfer, culture, detachment by trypsinization, freezing half of each subclone, treatment of the other half with mitomycin C or with gamma rays, incubation of chicken keratinocytes on each treated subclone, culture, fixing and staining with rhodamine B, and selection of the subclone on which there are the largest number of keratinocyte colonies of the largest size.

2. The culture medium as claimed in claim 1, wherein the proportion by weight of chicken serum relative to the total weight of the culture medium is between 0.5 and 50%.

3. The culture medium as claimed in claim 1, wherein the 3T3 cells have been inactivated by an antimitotic treatment selected from treatment with mitomycin C or irradiation with gamma rays.

4. The culture medium as claimed in claim 1, wherein the culture medium comprises one or more of the following constituents: inorganic salts, vitamins, hormones and growth factors.

5. The culture medium as claimed in claim 1, wherein the culture comprises one or more of the following constituents: inorganic salts, amino acids, vitamins, fatty acids, glucose, a buffer, phenol red, EGF (epidermal growth factor), $T_3$, hydrocortisone, insulin, cholera toxin, transferrin and adenine.

6. An avian keratinocyte culture comprising a culture medium that comprises chicken serum and a culture support comprising inactivated fibroblasts.

7. The keratinocyte culture as claimed in claim 6, wherein the culture medium that comprises chicken serum and a culture support comprising inactivated fibroblasts comprises inactivated 3T3 cells of the cell line registered in the ATCC collection under the number CCL92.

8. The keratinocyte culture as claimed in claim 7, wherein the keratinocytes are chicken keratinocytes.

9. A method of culturing avian keratinocytes, comprising:
(i) preparing a suspension of the keratinocytes;
(ii) inoculating said keratinocytes into a culture medium comprising chicken serum and a culture support comprising inactivated fibroblasts; and
(iii) incubating said keratinocytes in the culture medium.

10. The method as claimed in claim 9, wherein the culture medium comprises a chicken serum and a culture support comprising inactivated 3T3 cells of the cell line registered in the ATCC collection under the number CCL92.

11. The method of culture as claimed in claim 9, wherein at the end of step (iii), the keratinocytes derived from the culture are recovered and a further culture cycle is applied to them according to steps (ii) and (iii).

12. The method of culture as claimed in claim 11, comprising at most 30 cell culture cycles.

13. A method of propagating a virus in vitro, comprising:
(i) infecting keratinocytes with the strain of the virus;
(ii) placing the infected keratinocytes in culture according to the method of claim 9; and
(iii) extracting the virions produced in step (ii).

14. The method as claimed in claim 13, comprising a step of lyophilization of the virions.

15. The method as claimed in claim 13, wherein the avian keratinocytes are chicken keratinocytes.

16. The method as claimed in claim 13, wherein the virus is selected from (Marek's Disease Virus) and FPV (Fowlpox Virus).

17. A method for the preparation of a medicine for the prevention or treatment of Marek's disease, comprising propagating MDV by a method according to claim 13, and introducing the virion obtained into a pharmaceutically acceptable carrier.

* * * * *